(12) United States Patent
Gimelli et al.

(10) Patent No.: US 10,137,298 B2
(45) Date of Patent: Nov. 27, 2018

(54) HAND-HELD DEVICE FOR ELECTRICALLY POWERED SKIN TREATMENT

(71) Applicant: Swiss Spa System Ltd., Hong Kong (CN)

(72) Inventors: Bruno Gimelli, Zollikofen (CH); James N. Doyle, Jr., Ft. Myers, FL (US)

(73) Assignee: Swiss Spa System Ltd., Hong Kong (CN)

( * ) Notice: Subject to any disclaimer, the term of this patent is extended or adjusted under 35 U.S.C. 154(b) by 692 days.

(21) Appl. No.: 14/761,266

(22) PCT Filed: Jan. 16, 2014

(86) PCT No.: PCT/EP2014/000114
§ 371 (c)(1),
(2) Date: Jul. 15, 2015

(87) PCT Pub. No.: WO2014/111260
PCT Pub. Date: Jul. 24, 2014

(65) Prior Publication Data
US 2015/0360024 A1    Dec. 17, 2015

(30) Foreign Application Priority Data

Jan. 16, 2013    (DE) .................... 20 2013 000 390 U

(51) Int. Cl.
*A61N 1/32*    (2006.01)
*A61H 23/02*    (2006.01)
(Continued)

(52) U.S. Cl.
CPC ............. *A61N 1/328* (2013.01); *A61H 7/005* (2013.01); *A61H 23/02* (2013.01); *A61N 1/30* (2013.01);
(Continued)

(58) Field of Classification Search
CPC .......... A61N 1/328; A61N 1/322; A61N 1/30; A61N 1/26; A61H 23/02; A61H 7/005;
(Continued)

(56) References Cited

U.S. PATENT DOCUMENTS

| 5,514,167 A | 5/1996 | Smith et al. |
| 5,607,461 A | 3/1997 | Lathrop |

(Continued)

FOREIGN PATENT DOCUMENTS

| DE | 696 32 692 T2 | 6/2005 |
| EP | 2 384 789 A1 | 11/2011 |

(Continued)

OTHER PUBLICATIONS

PCT/EP2014/000114, International Search Report (PCT/ISA/220 and PCT/ISA/210) dated Mar. 31, 2014, enclosing Written Opinion of the International Searching Authority (PCT/ISA/237) (Seven (7) pages).

(Continued)

*Primary Examiner* — Mark W Bockelman
(74) *Attorney, Agent, or Firm* — Crowell & Moring LLP

(57) ABSTRACT

A hand-held device for electrically powered skin treatment is disclosed. The device includes a first outer electrode, a second outer electrode, and a plurality of rechargeable batteries. The plurality of batteries are disposed in a compartment where the compartment is covered by a shell-like housing cover and where an outside of the housing cover is a section of an exterior area of a device housing. The compartment is covered by a removable compartment cover where an inner side of the compartment cover is directed toward the plurality of batteries in the compartment and where a connector socket with at least two poles is disposed on an outer side of the compartment cover. The compartment (Continued)

Figure 1:
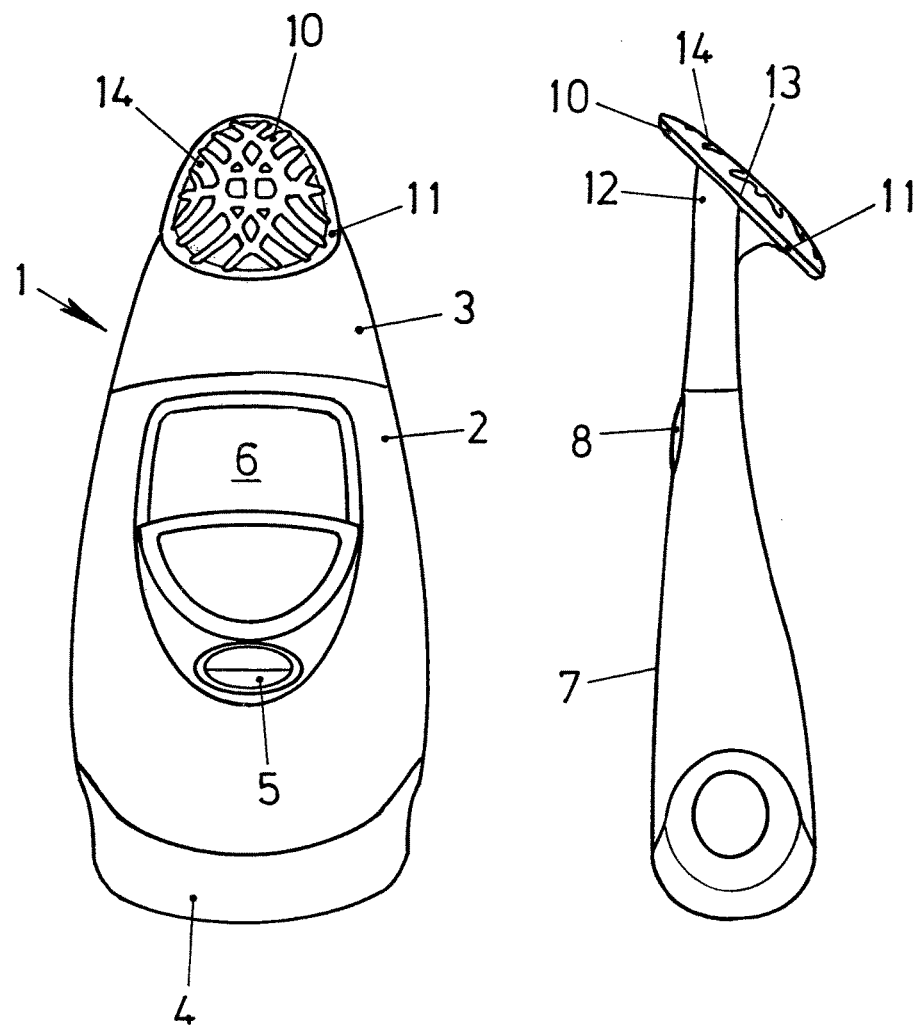

cover is located within the housing cover. A charging circuit is coupled to the plurality of batteries.

10 Claims, 4 Drawing Sheets

(51) Int. Cl.
*A61N 1/30* (2006.01)
*A61H 7/00* (2006.01)
*A61N 1/26* (2006.01)

(52) U.S. Cl.
CPC .......... *A61N 1/322* (2013.01); *A61H 2201/10* (2013.01); *A61H 2201/5035* (2013.01); *A61H 2201/5043* (2013.01); *A61N 1/26* (2013.01)

(58) Field of Classification Search
CPC .... A61H 2201/5043; A61H 2201/5035; A61H 2201/10
See application file for complete search history.

(56) References Cited

U.S. PATENT DOCUMENTS

| | | |
|---|---|---|
| 6,119,038 A | 9/2000 | Cook |
| 2001/0034544 A1 | 10/2001 | Mo |
| 2005/0278001 A1 | 12/2005 | Qin et al. |
| 2007/0129759 A1 | 6/2007 | Colthurst |

FOREIGN PATENT DOCUMENTS

| | | |
|---|---|---|
| GB | 2 390 022 A | 12/2003 |
| WO | WO 01/03638 A1 | 1/2001 |
| WO | WO 2005/087308 A1 | 9/2005 |

OTHER PUBLICATIONS

German Search Report issued in counterpart German Application No. 20 2013 000 390.1 dated Jul. 11, 2013, with English translation (Thirteen (13) pages).

HAND-HELD DEVICE FOR ELECTRICALLY POWERED SKIN TREATMENT

The invention relates to a hand-held device for electrically powered skin treatment, comprising:
- a first outer electrode, which is in contact with a hand when the device is held in the user's hand for use,
- a second outer electrode, which can be placed on the area of skin to be treated, and
- batteries, the poles of which are electrically connected to the electrodes during operation of the device,
- a compartment for accommodating the batteries, whereby the compartment is covered by a shell-like housing cover whose outside forms a section of the exterior area of the device housing.

A device of this type is described in WO 2005/087308 A1. To use the device, the user picks it up and places a cap functioning as a second electrode on the areas of skin to be treated. An electrically conductive contact to the hand is produced by the first electrode, and an electrically conductive contact to the area of skin to be treated is produced by the second electrode. Since the two electrodes are each connected to a pole of an electrical energy source, an electric circuit is produced which includes the user's body, wherein a positive or a negative electric current flows from the cap into the area of skin to be treated, depending on polarity.

This can be used to increase the efficacy of treatment creams and cleansing creams, since the active ingredients of a treatment cream are transported into the skin by means of the electric current and, with opposite polarity, pollutants are transported out of the skin into a cleansing cream.

The known device is battery-operated. In general, the batteries used do not have a very high capacity because batteries of a bigger capacity would raise the weight of the device which would mean an additional burden on the user when using the device.

Basically, it is known to provide such devices with rechargeable batteries and to provide a battery charger for charging the batteries. However, such battery chargers are often mislaid so that they are not at hand for the user when he needs one.

Hence, the invention is based on the object of adapting the known device in such a way that it is always usable, whereby no loss of comfort in the use of the device is caused.

To solve this problem, the invention proposes that
- the batteries are rechargeable batteries,
- a charging circuit is provided,
- the compartment for accommodating the batteries is covered by a removable compartment cover whose inner side is directed to the batteries in the compartment and on whose outer side a connector socket with at least two poles is arranged, and
- the compartment cover is located within the housing cover.

By use of the mentioned means, it is achieved that the batteries can be charged by connecting them via the connector socket to a power source, whereby the built-in charging circuit controls the charging process. For this purpose, the housing cover is removed so that the connector socket is exposed for connecting it with a charging cable.

A connector socket, which allows a current supply, is a connector socket according to the USB standard. This is frequently used in particular in the field of computers. Hence, the device can then be connected easily via a USB cable to a computer for charging the batteries.

To protect the batteries against humidity and to still allow easy access to the connector socket, the invention proposes that the upper end of the compartment is formed by a circumferential web, that the housing cover has, on its inner side, a circumferential counter web of the same contour as the web, whereby the counter web encloses the web on its outer side, and that the compartment cover is arranged inside the counter web.

Furthermore, it is intended to use the compartment cover to also fix the batteries in the compartment. For this purpose, the invention proposes that the compartment cover abuts the inner side of the housing cover.

A particularly simple arrangement is achieved if the compartment cover has an outer contour which corresponds to the inner contour of the web, so that the compartment cover lies inside the compartment.

The 2-pole connector socket or the USB connector socket, respectively, is accommodated in a space-saving way if the compartment cover forms a connector casing on its outer side which is open to the underside of the compartment cover and which has, in one of its side walls, a casing opening, and that in the connector casing a connector board with the connector socket is inserted, whereby the opening for the connector socket lies in front of the casing opening.

The charging circuit can be arranged on the connector board.

The device also has a user-operated switching device which establishes the electrical connection of the power source to the electrode and which is arranged on a main board inside the device. Hence, the charging circuit can also be accommodated, alternatively, on the main board.

To keep the interval between charging of the batteries as long as possible, it must be ensured that the power consumption of the device is minimised to the greatest extent possible. This is in particular relevant if the device comprises a vibrator that causes the second electrode, which is placed on the skin area to be treated, to shake.

In order to minimise the power consumption of such a device in which a vibrator is arranged in the vicinity of the second electrode, the invention provides that
- the vibrator's drive is connected to the batteries in a switchable manner, and provides
- a device for detecting a current flow through the second electrode,
- a switch in the connection of the drive of the vibrator to the batteries, and
- a control device for the switch, wherein the control device is designed in such a manner that the switch is only closed when a current flows through the second electrode.

In other words, the vibrator is switched on only if the second electrode is placed onto the skin area to be treated and via the second electrode a current flows through the skin. This current flow is detected and used by a control device in order to activate the switch.

The device can be implemented electronically. This means that the switch is designed as a transistor.

The described features for the switching operation of the vibrator's drive may also be used with devices which do not have means for loading the batteries and in which the batteries are accommodated in a different way than described above. Hence, the features for the switching operation of the vibrator's drive form an independent invention.

In the following, the invention is explained in more detail with reference to an exemplary embodiment.

Figure 2:
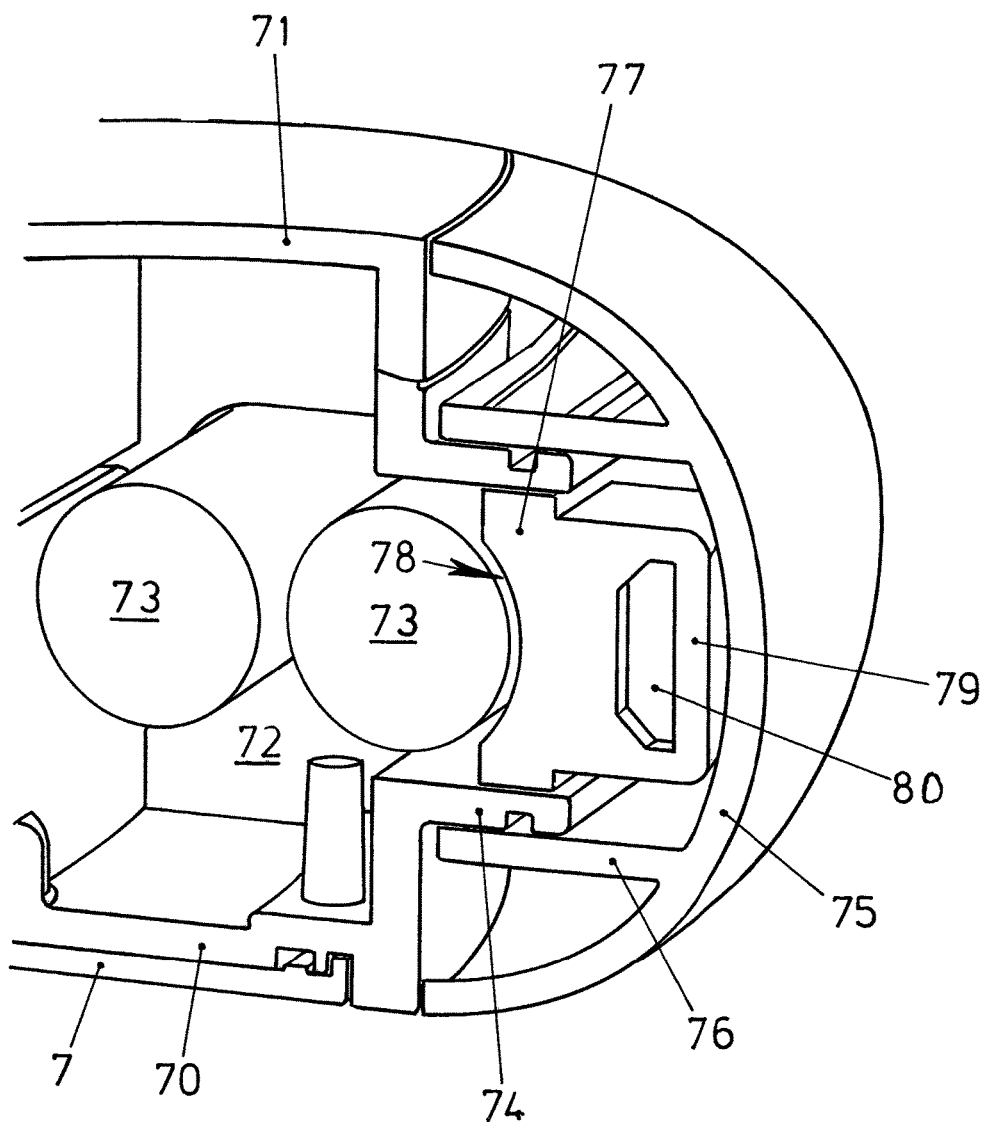
Figure 3:
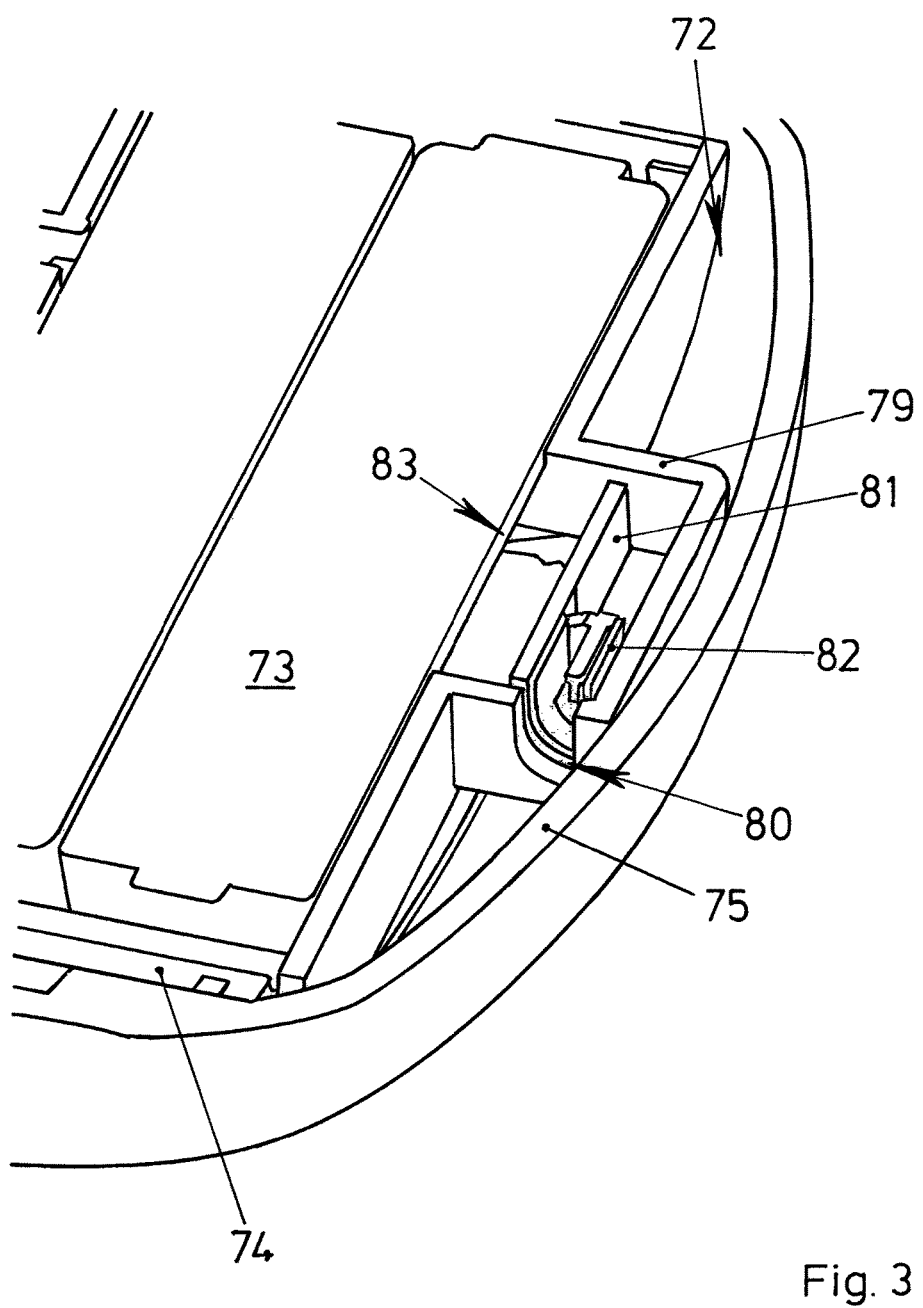
Figure 4:
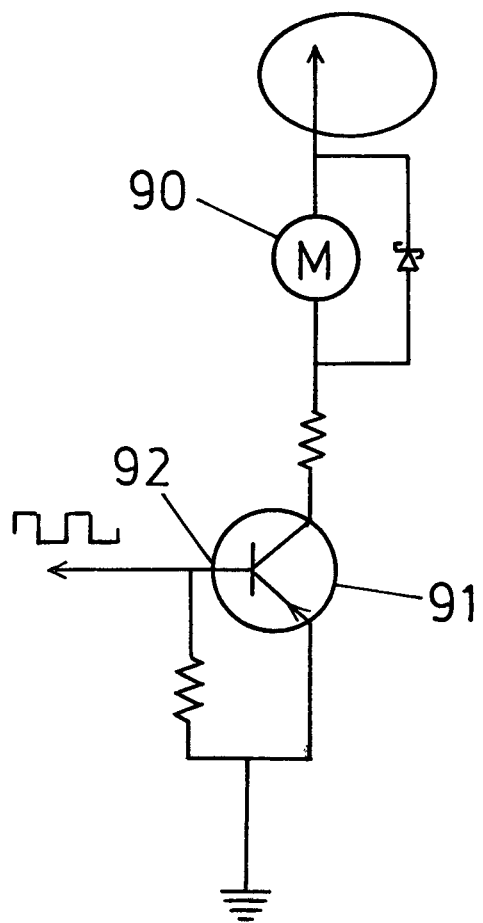

FIG. 1 shows two perspective views (front and lateral) of a device according to the invention which comprises a hand-held base and a cap with a platform to be laid on the skin to be treated, FIG. 2 shows a sectional view through a battery compartment of the device, a compartment cover and a housing cover lying above the compartment cover, FIG. 3 shows a sectional view through the compartment cover for the compartment with a USB connector socket, and FIG. 4 shows a circuit for controlling the vibrator motor.

Reference is first made to FIG. 1. As shown in the two views in FIG. 1, the device 1 according to the invention is approximately as large as the palm of a hand and has a shallow, rectangular design. It consists of a base 2 and a cap, which works as a second electrode 3 for contacting the skin, fitted thereon. A compartment 4 for accommodating batteries, which in this exemplary embodiment serve as the energy source to operate the device 1, is located at the lower, short end of the base 2.

The exchangeable cap 3 is fitted on the opposite, upper short end of the base 2, this end being narrower than the lower end. A button 5 for selecting a treatment program is arranged on the front side of the base 2, the selected treatment program being shown on a display 6 positioned there above. A first electrode 7 having a large surface area is located on the rear side and, above this, a press key 8 for actuating a catch, by means of which the cap 3 is held on the base 2.

Two tongues 10, 11 are attached to the upper edge of the cap 3 and together form a platform 13 which is inclined to the base 12 of the cap 3. The upper face of the platform 13 forms a continuous surface which can be placed on the skin and is provided with ribs 14.

As shown in FIG. 2, the housing of the device 1 comprises two half shells 70, 71 that are put together to form a closed housing, wherein the bottom region of the housing is essentially formed by an edge section of one of the half shells 70. In this edge, access to a compartment 72 is provided, into which compartment 72 rechargeable batteries 73 are inserted. The compartment 72 is formed by a circumferential web 74 on the edge section of the half shell 70. In the compartment 72, the batteries 73 are situated side-by-side and antiparallel to each other.

A half-shell-shaped housing cover 75 covers the compartment 72. For this purpose, said housing cover 75 on its inner side also comprises a circumferential counter-web 76 which is clipped onto the web 74 on the half shell 70. In this arrangement, the outside contour of the housing cover 75 is shaped in such a manner that a smooth transition to the outer contours of the half shells 70, 71 is formed.

In the compartment 72 itself, a compartment cover 77 is also provided that rests against the batteries 73 and for this purpose on its inner side comprises a trough-shaped indentation 78 and which on its outer side comprises a recess that forms a connector casing 79. The connector casing 79 rests against the inner side of the housing cover 75 so that in this manner a retaining force is exerted on the batteries 73 when the housing cover 75 with its counter-web 76 is clipped onto the circumferential web 74.

As can be seen from FIG. 3, the connector casing 79 is hollow and is open towards the underside of the compartment cover 77. On a wall of the connector casing 79, there is a casing opening 80. A connector board (81) with a USB connector socket 82 is inserted in the connector casing 79 in such a manner that the opening for the connector is situated in front of the casing opening 80. The connector board 81 or the connector socket 82 on the connector board 81 is connected via a cable 83 with the batteries 73 or with a main board (not shown here) in the base 2, on which the control circuit for the device 1 is arranged.

The cables 83 have a sufficient length so that the compartment cover 77 can be removed for inserting and replacing the rechargeable batteries 73 and also for reaching the connector casing 79, when—for the purpose of charging the batteries—these are connected via a USB cable with a power supply which is, for example, in a computer or laptop. The USB standard namely not only allows for the transfer of signal streams but also electrical currents up to 100 mA (according to the new USB-3 specification also transfer rates up to 900 mA) with a voltage of 5 V for the electricity supply of the particular device connected with the USB connector.

The charging circuit can be—if possible—arranged on the connector board, but it can also be arranged on the main board.

Rechargeable batteries are particularly of advantage if the device, in addition to the supply of electricity to the electrodes, also has a vibrator with which the second electrode 3 (cap), which is to be placed on the skin, is caused to vibrate.

In order to reduce the power consumption of the device, an electronic circuit, that is shown in FIG. 4, is provided, with which the vibrator's drive is only switched on if an electric current flows through the second electrode 3.

As can be derived from FIG. 4, the drive 90 of a vibrator is connected in series with the collector/emitter/path of a transistor 91. A control voltage is applied to the base 92 of the transistor 91. If this control voltage is present, the transistor connects through, and consequently current flows through the drive. If no voltage is present at the base 92, the transistor 91 blocks, and consequently the drive 90 is switched off.

The switching voltage on the base 92 is supplied by a control circuit which by means of a detector detects whether a current flows to the second electrode.

This can be implemented is a simple way, for example, in that a resistor is placed in the current loop of the second electrode, whereby the voltage drop at this resistor is used to generate a voltage signal for the base 92 of the transistor 91.

LIST OF REFERENCE CHARACTERS

| | |
|---|---|
| 1 | Device |
| 2 | Base |
| 3 | Second electrode/Cap |
| 4 | Compartment |
| 5 | Button |
| 6 | Display |
| 7 | First electrode |
| 8 | Press key |
| 10 | Tongue |
| 11 | Tongue |
| 12 | Base of a cap |
| 13 | Platform |
| 14 | Ribs |
| 70 | Half shell |
| 71 | Half shell |
| 72 | Compartment |
| 73 | Batteries |
| 74 | Web |
| 75 | Housing cover |
| 76 | Counter-web |
| 77 | Compartment cover |
| 78 | Indentation |
| 79 | Connector casing |

-continued

| | |
|---|---|
| 80 | Casing opening |
| 81 | Socket board |
| 82 | Connector socket |
| 83 | Cable |
| 90 | Drive |
| 91 | Transistor |
| 92 | Base |

The invention claimed is:

1. A hand-held device for electrically powered skin treatment, comprising:
 a first outer electrode which is contactable with a hand of a user when the device is held in the hand for use;
 a second outer electrode which is placeable on an area of skin to be treated;
 at least one battery, wherein the at least one battery is electrically connected to the first outer electrode and the second outer electrode during operation of the device and wherein the at least one battery is rechargeable;
 a compartment, wherein the at least one battery is disposed in the compartment, wherein the compartment is covered by a shell-like housing cover, and wherein an outside of the housing cover is a section of an exterior area of the device housing;
 wherein the compartment is covered by a removable compartment cover, wherein an inner side of the compartment cover is directed toward the at least one battery in the compartment and wherein a connector socket with at least two poles is disposed on an outer side of the compartment cover;
 wherein the compartment cover is located within the housing cover; and
 a charging circuit coupled between the at least one battery and the at least two poles of the connector socket.

2. The device according to claim 1, wherein the connector socket is a Universal Serial Bus (USB) connector socket.

3. The device according to claim 1, wherein an upper end of the compartment is formed by a circumferential web, wherein the housing cover has on an inner side a circumferential counter web that has a same contour as the circumferential web, wherein the circumferential counter web encloses the circumferential web on an outer side of the circumferential web, and wherein the compartment cover is disposed inside the circumferential counter web.

4. The device according to claim 3, wherein the compartment cover abuts an inner side of the housing cover.

5. The device according to claim 4, wherein the compartment cover has an outer contour which corresponds to an inner contour of the circumferential web such that the compartment cover is disposed inside the compartment.

6. The device according to claim 1, wherein the compartment cover forms a connector casing on an outer side of the compartment cover, wherein the connector casing has a casing opening, and wherein a connector board with the connector socket is disposed in the connector casing such that an opening of the connector socket lies in front of the casing opening.

7. The device according to claim 6, wherein the charging circuit is disposed on the connector board.

8. The device according to claim 1, further comprising a user-operated switching device, wherein an electrical connection of a power source to the first and second electrodes is enabled by the switching device, wherein the switching device is disposed on a main board, and wherein the charging circuit is disposed on the main board.

9. The device according to claim 1, further comprising:
 a vibrator disposed in a vicinity of the second electrode, wherein a drive of the vibrator is connected to the at least one battery;
 a current flow detection device, wherein a current flow through the second electrode is detectable by the current flow detection device;
 a switch disposed in the connection of the drive of the vibrator to the at least one battery; and
 a control device, wherein the control device controls the switch such that the switch is only closed when a current flows through the second electrode.

10. The device according to claim 9, wherein the switch is a transistor.

* * * * *